United States Patent [19]

Perry et al.

[11] Patent Number: 4,933,468

[45] Date of Patent: Jun. 12, 1990

[54] PREPARATION OF AMIDE-IMIDES

[75] Inventors: Robert J. Perry; S. Richard Turner, both of Pittsford, N.Y.

[73] Assignee: Eastman Kodak Company, Rochester, N.Y.

[21] Appl. No.: 405,259

[22] Filed: Sep. 11, 1989

Related U.S. Application Data

[63] Continuation-in-part of Ser. No. 297,788, Jan. 17, 1989.

[51] Int. Cl.$^5$ ............................................. C07D 209/48
[52] U.S. Cl. .................................... 548/476; 546/200; 546/201; 546/208; 548/539; 560/97; 560/206; 562/406
[58] Field of Search ............................... 548/476, 539; 260/544 A; 546/200, 201, 208; 560/97, 206; 562/406

[56] References Cited

PUBLICATIONS

Yoneyama et al., Macromolecules, (1988), 21, pp. 1908–1911.
R. F. Heck, Palladium Reagents in Organic Syntheses, Academic Press, New York, N.Y., (1985), pp. 348–359.
Mori et al., Heterocycles, 13, (1979), pp. 329–332.

*Primary Examiner*—Anton H. Sutto
*Assistant Examiner*—D. D. Carr
*Attorney, Agent, or Firm*—Robert A. Linn

[57] ABSTRACT

Amide-imides are prepared by reacting carbon monoxide with an ortho dihalide aromatic compound or a cis-1,2-vinyl dihalide having an isolated halogen function, and with an amine, in the presence of palladium catalyst and a base. The process is preferably conducted in the presence of a dipolar aprotic solvent as a liquid reaction medium.

5 Claims, No Drawings

PREPARATION OF AMIDE-IMIDES

CROSS-REFERENCE TO RELATED APPLICATION

This application is a continuation-in-part of Application Ser. No. 297,788, filed Jan. 17, 1989.

FIELD OF THE INVENTION

This invention relates to amide-imides and to processes for their preparation. The amide-imides may be monomeric, oligomeric, or polymeric. The processes comprise palladium catalyzed carbonylations. Other catalysts can be used.

RELATED ART

Yoneyama et al, *Macromolecules* (1988) 21, pp. 1908–1911, discloses the synthesis of aromatic polyamides by palladium-catalyzed polycondensation of aromatic dibromides, aromatic diamines, and carbon monoxide.

The literature relating to the carbonylation of aromatic halides, and the formation of amides and other compounds by such a route, is summarized in Heck, R. F., *Palladium Reagents in Organic Syntheses*, Academic Press, New York, N.Y. (1985) pp. 348–359. The preparation of cyclic and acyclic imides by the process of this invention is not suggested by the above references.

Mori et al, *Heterocycles* 13, 329–332 (1979) discloses formation of monomeric cyclic imides and quinolone by the palladium catalyzed carbonylation of aryl and vinyl monobromides having an amine or amide group on a carbon atom adjacent to the carbon substituted with the bromide radical. The reference does not disclose the reaction of dibromides or diiodides.

SUMMARY OF THE INVENTION

This invention provides a method for the preparation of amide-imides. The products may be monomeric, oligomeric, or polymeric. The products may also contain amide groups and other functional groups.

The formation of imide groups which occurs in the process of this invention is illustrated by the following equations depicting the preparation of N-phenylphthalimide from diiodobenzene, aniline, and carbon monoxide. The illustrated process is conducted in the presence of palladium tetrakis(triphenylphosphine) (PdL₄), dimethylacetamide (DMAc), and 1,8-diazobicyclo-[5,4,0]undec-7-ene (DBU). The DMAc is used as a solvent; the DBU is a base for neutralizing by-product hydrogen halide. One possible mechanism is depicted by the following equations:

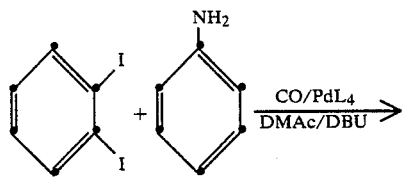

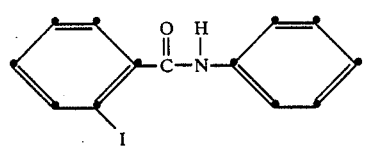

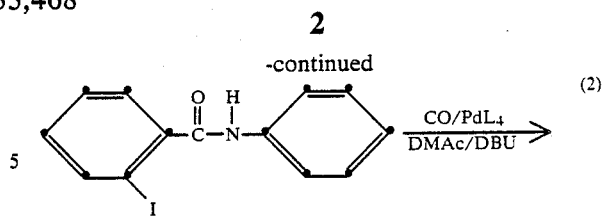

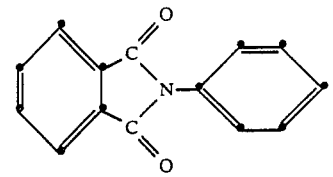

Although not bound by any theory, it is believed that the reactions depicted by Equations (1) and (2) may both proceed through an unisolated intermediate, formed by insertion of

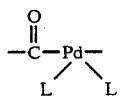

between the ring and the halide radical. Thus, for example, it is believed that the intermediate formed in Equation (2) has the formula:

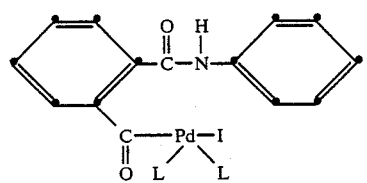

where L is a ligand such as carbon monoxide or triphenylphosphine. The above process suggests that to form an imide group, it is not necessary to use an aromatic orthodihalide reactant (i.e., an aryl compound with 1,2-dihalofunctionality) as depicted in the above example. More specifically, it suggests that one may use a cis-1,2-dihalovinyl compound, and react it with CO and a primary amine as illustrated by the following unbalanced, simplified equation:

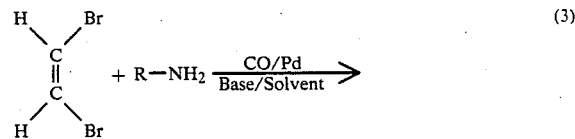

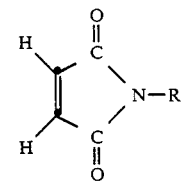

If the starting halo compound has a pair of halogen radicals as illustrated above plus another isolated halogen, i.e., a halogen not on a carbon atom adjacent to a halogen-substituted carbon, the product will have both amide and imide groups, as illustrated by the following, where Y is a linking bond or a bridging group.

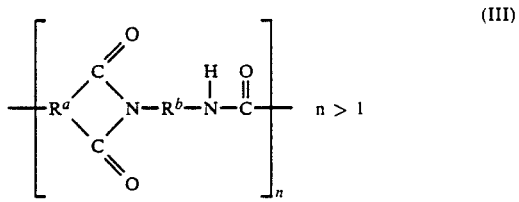

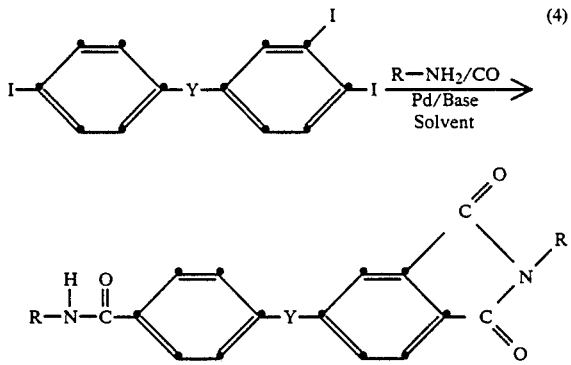

Oligomeric or polymeric products can be produced by reactions similar to the above; for example, by reacting carbon monoxide with a compound having two primary amine groups and a compound having one pair of halogen atoms and an isolated halogen atom. Similarly, oligomers or polymers can be made by polymerizing a compound having an amino group, an isolated halogen, and a pair of adjacent, aromatic, or vinylic halogens, in the presence of CO, palladium catalyst, base, and solvent.

The monomeric, oligomeric, and polymeric compounds can be used as chemical intermediates. The oligomeric and polymeric amide-imides have the utilities known for these classes of materials. For example, the amide-imides can be used as engineering plastics.

It will be noted from the above equations that the process of this invention for preparing amide-imide polymers and oligomers does not employ reactants commonly used in the art for preparing such materials. Some of the prior art reactants, e.g., anhydrides are susceptible to hydrolysis. The reactants used in the present process are not. Furthermore, it will also be noted that water is not formed as a by-product in the instant process. Hence, the process of this invention has inherent advantages over known, prior processes for amide-imide formation.

For the purpose of description of this invention, the products of the process are designated "imide-amides" or alternatively, "imide/amides," "amide/imides", or "amide-imides".

DESCRIPTION OF PREFERRED EMBODIMENTS

This invention comprises embodiment (1) a process for the preparation of a cyclic imide/amide, said process comprising reacting carbon monoxide and a primary amine with a vicinal organo dihalide, having an isolated halogen, i.e., a halide which has two halogen radicals (selected from bromide and iodide) on adjacent carbon atoms and a halogen (selected from bromide and iodide) on a carbon atom non-adjacent to the aforesaid adjacent carbons, said process being conducted in the presence of a catalytic quantity of a palladium catalyst, an ether or dipolar aprotic solvent, and a base for neutralizing by-product hydrogen halide.

As indicated above, the preferred processes for preparing oligomers and polymers employ difunctional starting materials. Products made from such starting materials are generally linear and tractable. If one or more of the reactants are trifunctional, non-linear products can be formed. Such products generally are less tractable, i.e., less capable of producing useful end products. Hence, in many instances, processes of this invention which utilize trifunctional starting materials are less preferred.

Cyclic imide/amide oligomeric and polymeric products of the process of this invention have the formula:

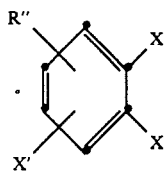

(III)

wherein $R^a$ is the moiety from the halide reactant and $R^b$ is the moiety from the primary diamine reactant.

In the above formula, n is an integer having a value of 2 to about 500 or higher, more preferably from 2 to about 350. For the purpose of this invention, when the value of n is from 2 to about 10, the products are referred to as "oligomers"; when the value of "n" is higher, the products are referred to as "polymers".

The reactants from which these products are derived are discussed and illustrated below.

Some aryl ortho halides useful in this invention as starting materials have the formula:

wherein each X is independently selected from bromine and iodine, X' is a bromide or iodide substituent (—Br, or —I) bonded to a carbon atom non-adjacent to a carbon atom bonded to X and R" is an inert substituent.

As set forth more fully below, the halide need not be a benzenoid compound as depicted above. Rather, it may be a halide derivative of a fused ring compound. Alternatively, the halide may have two or more aryl groups bonded together or linked by a linking group. The halides may have additional substitution.

For example, in a fused ring compound, or in a compound having two linked aryl groups, or two bridged aryl groups, there may be two pair of halogens ortho to each other plus a non-ortho halogen. Reaction of such a compound with a compound having a plurality of primary amino groups according to this invention will yield a polymeric or oligomeric cyclic imide-amide.

Stated another way, a reactant employed in this invention may have a pair of halogens ortho to each other and one or more additional halogens which are "isolated", i.e., not vicinal, i.e., not ortho or adjacent to another halogen. As stated above, reaction of this type of compound, according to this invention, with a reactant having two or more primary amino groups will yield a polymeric or oligomeric material having imide and amide linkages.

From the above it can be seen that a wide variety of halides can be reacted according to this invention. They may be exemplified by compounds having one of the following general formulas wherein X is bromide or iodide and Y is carbon or a hetero atom such as, but not limited to, oxygen, nitrogen, sulfur, phosphorous, silicon, etc. In the formulas, X' is an "isolated halogen selected from bromine and iodine".

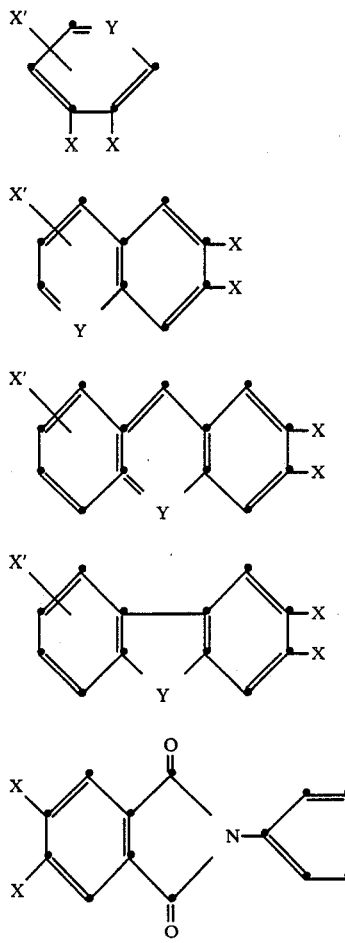

It will be apparent to a skilled practitioner that ortho dihalo derivatives of other fused ring systems are also applicable in this invention, and that the ortho halogen pair may be in positions other than illustrated above. Similarly, the "isolated" halogen X' in the multi-ring compounds may appear on a ring other than the ring depicted in the above formulas.

In addition, the pair of ortho halogens may be within compounds having two or more isolated aryl rings which are bonded together, such as ortho dihalo derivatives of biphenyl and terphenyl. Also, the pair of ortho halogens may be substituted on rings within compounds having two or more fused ring systems that are bonded together or that have a fused ring system bonded to a benzenoid nucleus as in the following examples:

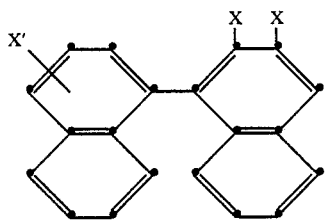

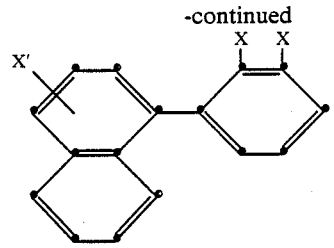

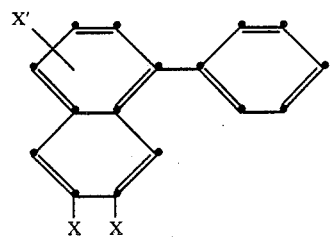

Again X' need not appear on the ring shown, but may appear on any other ring in the molecule.

In accordance with the description above, additional reactants employed in this invention are exemplified by the following compounds:

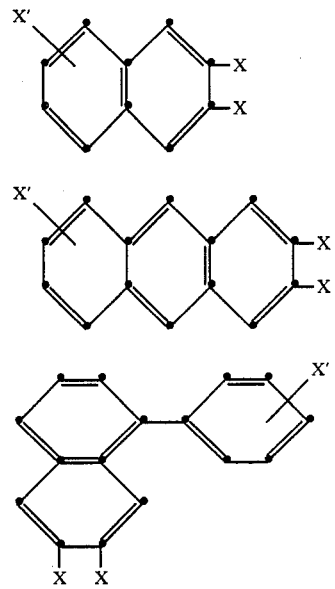

and also by compounds similar to the above wherein X' is on a ring other than the ones shown above.

Reactants analogous to the above can have the rings or fused ring systems connected by a bridging group rather than bonded together by a carbon-to-carbon bond. Typical bridging groups are:

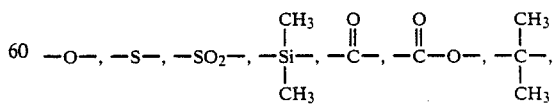

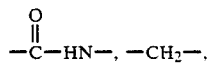

and $-CH_2-(CH_2)_n-CH_2-$, wherein n is from about 1 to about 6 or higher, and the like. Such reactants are illustrated by the following formulas, wherein Y' is a bridging group of the type illustrated above or phenylene, vinylene, carbonate, or

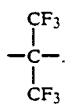

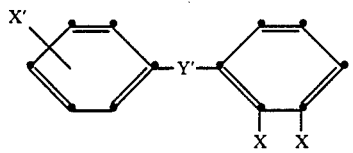

In addition, the bridging group Y' can bridge a benzene nucleus with a fused ring system, or two fused ring systems:

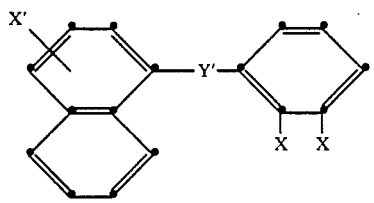

Other fused ring systems similar to those illustrated above can be linked by a bridging group Y', and substituted with one more pair of ortho halogens.

Of the halo reactants mentioned above, it is preferred to use iodo aromatic compounds.

As with all the other polyhalo reactants illustrated above, the isolated halogen X' can appear on a ring other than that shown by the above formula.

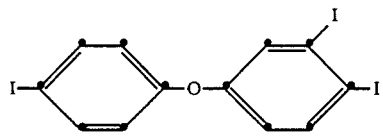

Cis-vinyl dihalides have been mentioned above as reactants in this invention. The vinyl linkage may be in a chain or ring, e.g., in cyclopentene. Two cyclopentene groups can be bonded together by a carbon-to-carbon bond, or linked by a bridging group. Alternatively, the cyclopentene ring can be a substituent on an aryl nucleus as in

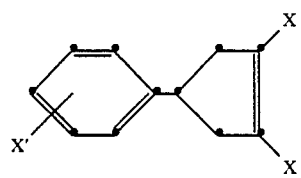

Preferably, the amine reactant is an alkyl or aromatic amine. It can be aniline, or alternatively be a primary or secondary amine derivative of one of the fused or bridged ring systems of the type illustrated above. Similarly, there may be two or more primary amino groups substituted on a benzenoid nucleus, or on a fused ring system or a bridged ring system.

Aliphatic primary amines can be used in this process. They may be saturated or unsaturated. They may also comprise one or more (non-aryl) rings or be acyclic. Preferably, the aliphatic amines are alkyl primary or secondary amines wherein the alkyl group or groups have up to about 10 carbon atoms. The alkyl groups may be branched or unbranched. Preferably the amines are liquids or solids that are soluble or dispersible in the reaction mixture.

Compounds having two or more primary amino groups within the molecule are illustrated by the following compounds:

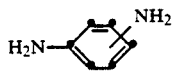

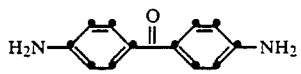

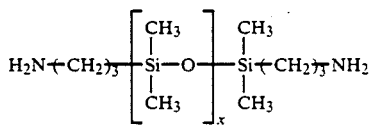

x = 1-50

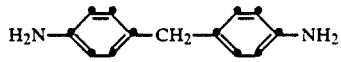

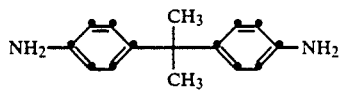

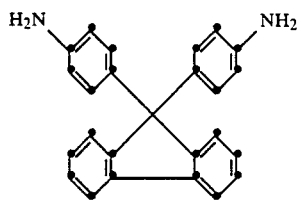

y = 1-10

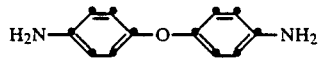

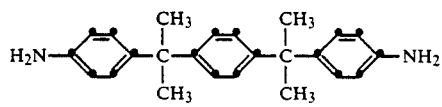

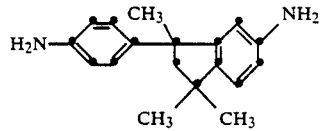

As can be seen by the above description, a wide variety of dihalo and amino reactants can be used in the processes of this invention. Preferably, such reactants are "stable" under the reaction conditions employed, i.e., they do not decompose to an unacceptable extent during the process of this invention. The organic materials used in this invention are also "suitable reactive", i.e., the process of this invention without entering into an unacceptable amount of undesirable side reaction(s). Thirdly, the organic reactants used in this invention be "sterically suitable", i.e., that they not be so bulky as to unduly retard the reaction by steric hindrance. Examples of such reactants have been given above.

The amine and halide reactants are contacted with carbon monoxide. The CO may be at atmospheric pressure or at a higher pressure. Carbon monoxide pressures in the range of from about 1 to about 200 atmospheres or higher can be used in the process.

Pressures lower than atmospheric can be used if desired, but generally do not confer any advantage.

The process proceeds well when the reactants are contacted in stoichiometric amounts. However, it is not necessary to use stoichiometric quantities. An excess of one or more reactants can be used to control the average degree of polymerization. A convenient amount of excess is preferably used.

It is convenient to add an excess of carbon monoxide to the reaction zone. The excess of CO need not be measured; one may merely pressurize the vessel with CO to the desired reaction pressure.

When one of the organic reactants is used in excess, it is preferably used in an amount of from 1.001 to about 5 times the molar amount required by stoichiometry.

The process of this invention is conducted in the presence of a liquid reaction medium to facilitate contacting the reactants. A wide variety of organic compounds can be used for this purpose so long as the reaction medium is "inert", i.e., does not enter into the reaction in an undesired way. It is preferred that the reaction medium dissolve the reactant(s) to an appreciable extent. For preparation of monomeric cyclic imides, an ether solvent can be used. A preferred solvent of this type is tetrahydrofuran or diglyme (2-methoxyethyl ether), or glyme (1,2-dimethoxy ethane). For preparation of oligomeric and polymeric products, a dipolar aprotic solvent is preferentially employed. Such solvents are characterized by the lack of acidic, easily abstractable hydrogens and are highly polar molecules. Typical dipolar aprotic solvents are dimethyl formamide, dimethylacetamide, dimethylsulfoxide, hexamethylphosphoramide, and the like.

The amount of liquid reaction medium is not critical. Generally, one uses enough medium to facilitate the reaction. There is no real upper limit on the amount of reaction medium employed. However, practical limits are imposed by the size of the reaction vessel, the ease of separation of product(s) from the reaction medium, cost, and similar considerations. Generally, the amount of liquid reaction medium employed is within the range of from about 0.1 to about 800 volumes based on the volume of halo or vinyl aromatic employed.

The process of this invention is conducted in the presence of a catalyst. The catalyst is preferentially a palladium compound, where palladium is present in the zerovalent or divalent state. Other transition metal catalysts, e.g., nickel and cobalt catalyst can be used. The palladium catalysts generally have one or more ligands bonded to the palladium atom(s) by ionic or covalent bonds. Simple palladium salts such as $PdX'_2$ wherein $X'$ is Cl, Br or I can be used. Other representative palladium catalysts are listed below:

TABLE I

| Palladium Catalysts | |
|---|---|
| $Pd^{+2}$ | |
| $PdX_2$ | X = Cl, Br, I |
| $PdX_2L_2$ | X = Cl, Br, I |
| | L = $R_3P$, where R = alkyl or aryl |
| $Pd(OAc)_2$ | OAc = acetate |
| $Pd(OAc)_2L_2$ | OAc = acetate |
| $PdCl_2(RCN)_2$ | R = $CH_3$, Phenyl |
| $PhPdXL_2$ | X = Br, I |
| $PdCl_2(COD)_2$ | COD = cis,cis-1,5-cyclooctadiene |
| $Pd(acac)_2$ | acac = 2,4-pentanedionate |
| $Pd^{(o)}$ | |
| $PdL_4$ | |
| L = $R_3P$ where | |
| R = alkyl or aryl | |

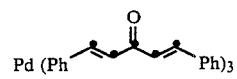

Pd (Ph~~~Ph)$_3$

It is contemplated that similar results can be obtained when other transition metal catalysts are employed, such as those containing nickel, rhodium, or ruthenium.

A catalytic amount of catalyst is employed. By "catalytic amount" is meant an amount of catalyst which catalyzes the reaction to the desired extent. Generally, the amount of catalyst is at least about 0.05 mole percent based on the amount of aryl or vinyl halide. There is no real upper limit on the amount of catalyst, this being defined by secondary conditions such as cost and ease of separation of the catalyst from products and unreacted reactants. A preferred catalytic amount is from about 0.005 to about 0.20 moles per mole of aryl or vinyl halide, more preferably from about 0.02 to about 0.10 mole per mole of halide reactant.

The process of this invention is preferably conducted in the presence of a base to neutralize by-product hydrogen halide. The base may be a tertiary amine such as tributylamine, pyridine, 1,8-diazobicyclo[5,4,0]-7-undecene (DBU) or have the formula:

$NR_3$ wherein each R is independently selected from lower alkyl groups having from about 2 to about 6 carbon atoms. The base may be immobilized on a cross-linked polymer such as cross-linked poly(vinylpyridine) beads. Alternatively, the base may be another type of basic substance which does not react with the reactants, e.g., a metal carbonate such as $K_2CO_3$ or a metal hydroxide such as $Ca(OH)_2$. Generally, one employs at least enough base to react with the by-product HX produced. An excess can be used, if desired.

As with the reactants, solvents and catalysts, a skilled practitioner will recognize that the exact structure of the base is not critical, and the examples of compounds set forth above are merely illustrative and not-limiting examples of materials that can be used in this invention. A skilled practitioner will recognize that other materials can be substituted in this invention to achieve similar results.

The process of this invention is preferably conducted at a temperature within the range of from about ambient to about 250° C. A preferred temperature range is from about 60° C. to about 160° C. A skilled practitioner will recognize that the reaction temperature is not critical, and that temperatures outside this range can be employed, if desired. Generally, one selects a reaction temperature which affords a reasonable rate of reaction and which does not give an undue amount of decomposition of products or reactants.

The reaction time is not a truly independent variable, but is dependent at least to some extent based on the other reaction parameters selected such as reactivity of the reactants, activity, and amount of catalyst, reaction temperature, pressure, and similar variables. Generally speaking, reaction times within the range of from about 0.1 to about 100 hours are used.

mmol), PdCl$_2$L$_2$ (19 mg, 0.027 mmol), PPh$_3$ (14 mg, 0.054 mmol) and DMAc (2.2 mL). After degassing, heating to 120° C., dissolution of reagents and subsequent addition of DBU (240 μL, 1.6 mmol) the vessel was charged with 95 psi CO and the reaction was allowed to proceed for 23 hours. At the end of this time the contents of the vessel were filtered through a filter aid, precipitated into methanol, washed with methanol and dired in vacuo to give 165 mg polymer (74%) as a gray solid. IV (0.25% in DMAc @ 25° C.)=0.16.

EXAMPLE 1

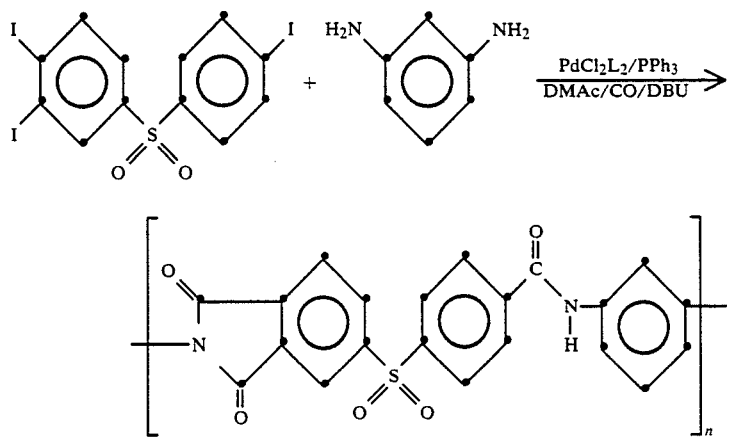

A Fischer-Porter bottle was charged with 3,4,4'-triiododiphenylsulfone (229 mg, 0.384 mmol), m-phenylenediamine (41.6 mg, 0.384 mmol), PdCl$_2$L$_2$ (27 mg, 0.038 mmol), PPh$_3$ (20 mg, 0.0.076 mmol) and DMAc (2.0 mL). After degassing, heating to 120° C., dissolution of reagents and subsequent addition of DBU (207 μL, 1.38 mmol) the vessel was charged with 95 psi CO and the reaction was allowed to proceed for 22 hours. At the end of this time the contents of the vessel were filtered through a filter aid, precipitated into methanol, washed with methanol and dried in vacuo to give 158 mg polymer (102%) as a gray solid. IV (0.25% in DMAc @ 25° C.)=0.19. IR(KBr) 1780, 1725 cm$^{-1}$ (imide C=O), 1660, 1550, 1300 cm$^{-1}$ (amide C=O), 1320, 1155 cm$^{-1}$ (SO$_2$).

IR(KBr) 1775, 1720 cm$^{-1}$ (imide C=O), 1645 cm$^{-1}$ (amide C=O), 1320, 1155 cm$^{-1}$ (SO$_2$NH).

Oligomeric and polymeric materials can be made by following the teachings of the above examples, and substituting for the reactants used in the examples, compounds which are polyfunctional, e.g., primary diamines, and aromatic and vinyl halides having at least one dihalo and one non-adjacent monohalo functionalities, of the type described and illustrated above. Generally speaking, polymeric products are produced instead of oligomers when the starting materials are more reactive, the reaction temperatures are higher, or the reaction is conducted for a longer time.

In the process of the above examples, the dimethyl acetamide solvent can be substituted with an ether such

EXAMPLE 2

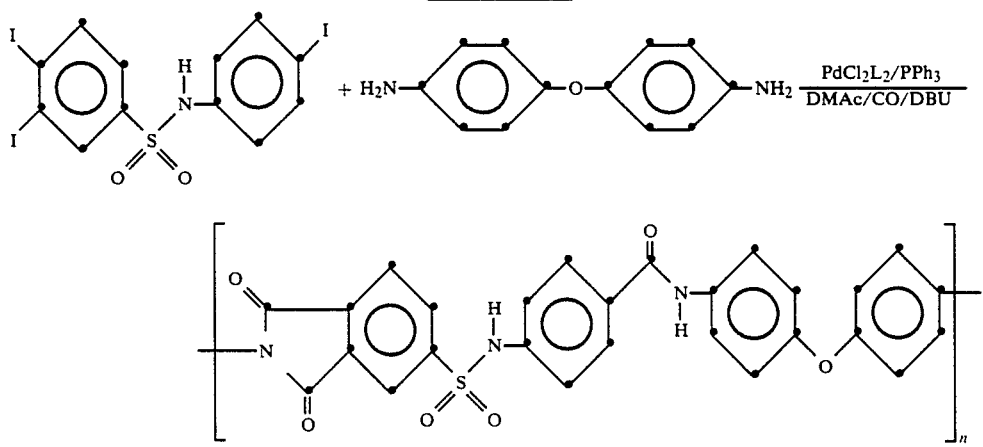

A Fischer-Porter bottle was charged with N-(4-iodophenyl)-3,4-diiodophenylsulfonamide (273 mg, 0.447 mmol), 4,4'-diaminodiphenylether (89.5 mg, 0.447 as those named above, or by N,N-dimethyl formamide, hexamethylphosphoramide, dimethylsulfoxide, 1,3-dimethyl-2-imidazolidinone, pyridine, and the like.

The DBU can be substituted with $K_2CO_3$, $Ca(OH)_2$, tri-butyl amine, pyridine, and the like.

The process can be conducted using $PdX_2$, $PdXL_2$, $Pd(OAc)_2$, $Pd(OAc)_2L_2$, $PdCl_2(C_6H_5CN)_2$, $PhPdXL_2$, $PdCl_2(COD)_2$, $Pd(acac)_2$, or $PdL_4$, and the like in an amount of from about 0.005 to about 0.20 per mole of halide.

A skilled practitioner familiar with the above-detailed description of the invention can make many modifications and substitutions without departing from the scope and spirit of the appended claims.

We claim:

1. A process for the prepartion of a monomeric imide-amide, said process comprising reacting a vicinal organic halide selected from the class consisting of aryl ortho dihalides and cis-1,2-vinyl dihalides wherein the halogens are selected from bromine and iodine with a primary amine and carbon monoxide; said vicinal halide having an isolated monohalo function wherein the halogen is selected from bromine and iodine, said process being conducted in the presence of a catalytic quantity of a palladium catalyst, a solvent, and a base to neutralize by-product hydrogen halide;

said aryl dihalides being further characterized by having from 6 to about 20 carbon atoms, said primary amine being selected from primary alkyl and aryl monoamines and diamines, said aryl amines having from 6 to about 20 carbon atoms, said alkyl amines having up to about 10 carbon atoms.

said solvent being an ether or a dipolar aprotic solvent, said base being a tertiary amine, and said process being conducted at a temperature of from about ambient to about 250° C.

2. Process of claim 1 wherein said halide is an iodide.

3. Process for the preparation of an imide/amide oligomer or polymer, said process comprising reacting carbon monoxide with an organic halide having a dihalo function and a monohalo function selected from the class consisting of aryl ortho dihalides and cis-1,2-dihalovinyl compounds having an isolated monohalo function wherein the halogens are independently selected from bromine and iodine, and a primary diamine, said process being conducted in the presence of a catalytic quantity of a palladium catalyst, a solvent, and a base to neutralize by-product hydrogen halide;

said aryl dihalides being further characterized by having from 6 to about 20 carbon atoms, said primary amine being selected from primary alkyl and aryl monoamines and diamines, said aryl amines having from 6 to about 20 carbon atoms, said alkyl amines having up to about 10 carbon atoms, said solvent being an ether or a dipolar aprotic solvent, said base being a tertiary amine, and said process being conducted at a temperature of from about ambient to about 250° C.

4. A process of claim 3 wherein said organo halide is 3,4,4'-triiododiphenylsulfone, and said diamine is m-phenylenediamine.

5. A process of claim 3 wherein said organo halide is N-(4-iodophenyl)-3,4-diiodophenylsulfonamide, and said diamine is 4,4'-diaminodiphenylether.

* * * * *